US011789483B2

United States Patent
Ruegsegger et al.

(10) Patent No.: US 11,789,483 B2
(45) Date of Patent: Oct. 17, 2023

(54) ADAPTIVE DRIVING DEVICE

(71) Applicant: Ohio State Innovation Foundation, Columbus, OH (US)

(72) Inventors: Mark Ruegsegger, Dublin, OH (US); Sandra Metzler, West Jefferson, OH (US); Luke Lemmerman, St. Mary's, OH (US); Jenna Tabbaa, Westlake, OH (US); Ilya Gulko, Richmond Heighls, OH (US); Kezhuo Wang, Los Angeles, CA (US); Riley Hulbert, Madison, WI (US); Lauren Mershad, Dayton, OH (US); Kaitlin Finch, Powell, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 223 days.

(21) Appl. No.: 17/434,660

(22) PCT Filed: Apr. 19, 2019

(86) PCT No.: PCT/US2019/028284
§ 371 (c)(1),
(2) Date: Aug. 27, 2021

(87) PCT Pub. No.: WO2020/176118
PCT Pub. Date: Sep. 3, 2020

(65) Prior Publication Data
US 2022/0171421 A1   Jun. 2, 2022

Related U.S. Application Data

(60) Provisional application No. 62/811,313, filed on Feb. 27, 2019.

(51) Int. Cl.
*G05G 1/01* (2008.04)
*A61F 4/00* (2006.01)
(Continued)

(52) U.S. Cl.
CPC ............... *G05G 1/01* (2013.01); *A61F 4/00* (2013.01); *B60K 35/00* (2013.01); *B60K 37/06* (2013.01);
(Continued)

(58) Field of Classification Search
CPC .. G05G 1/01; B62D 1/043; A61F 4/00; B60K 35/00; B60K 37/06; B60K 2370/131
See application file for complete search history.

(56) References Cited

U.S. PATENT DOCUMENTS 2,561,961 A    7/1951  White
4,476,954 A   10/1984  Johnson et al.
(Continued)

OTHER PUBLICATIONS

International Search Report and Written Opinion, issued by the International Searching Authority (ISA/US) in PCT Application No. PCT/US2019/028284 dated Jul. 2, 2019. 7 pages.
(Continued)

*Primary Examiner* — Thomas C Diaz
(74) *Attorney, Agent, or Firm* — Meunier Carlin & Curfman LLC

(57) ABSTRACT

Various implementations include an assistive driving device including a base, a first post, a second post, a third post, and a selector. The first post is for receiving a portion of a palm of a hand of a user and has a proximal end and a distal end. The second post has a proximal end and a distal end. The third post has a proximal end and a distal end. The proximal ends of the first, second, and third posts are coupled to the base. The second post and the third post are positioned to receive a portion of an arm of the user. The selector is spaced apart from the first post and positioned such that the selector is actuatable with a dorsum of the hand of the user.

20 Claims, 5 Drawing Sheets

(51) Int. Cl.
    *B60K 35/00*     (2006.01)
    *B60K 37/06*     (2006.01)
    *B62D 1/22*     (2006.01)

(52) U.S. Cl.
    CPC .......... *B62D 1/22* (2013.01); *B60K 2370/131* (2019.05); *B60K 2370/157* (2019.05)

(56) References Cited

U.S. PATENT DOCUMENTS

| | | | |
|---|---|---|---|
| 4,895,039 | A | 1/1990 | Hegg |
| 6,701,801 | B1 | 3/2004 | Wilson |
| 7,621,365 | B2 | 11/2009 | Egan |
| 10,149,730 | B2 * | 12/2018 | Sholev .............. A61B 17/2909 |
| 2001/0020140 | A1 | 9/2001 | Kramer |
| 2005/0023071 | A1 * | 2/2005 | Ahnafield ............. B60W 30/18 |
| | | | 74/471 R |
| 2005/0274563 | A1 | 12/2005 | Ahnafield |
| 2010/0235041 | A1 | 9/2010 | Aeberhard et al. |
| 2012/0285289 | A1 | 11/2012 | Walker et al. |

OTHER PUBLICATIONS

International Preliminary Report on Patentability issued for Application No. PCT/US2019/028284, dated Sep. 10, 2021.

\* cited by examiner

ADAPTIVE DRIVING DEVICE

CROSS REFERENCE TO RELATED APPLICATIONS

This application is a national stage application filed under 35 U.S.C. § 371 of PCT/US2019/028284 filed Apr. 19, 2019, which claims the benefit of U.S. Provisional Patent Application No. 62/811,313, filed Feb. 27, 2019, the content of which is incorporated herein by reference in its entirety.

BACKGROUND

One life-impacting problem for individuals with spinal cord injuries ("SCI") or that have limited hand function is the ability to control both a vehicle's steering wheel and secondary controls with one hand. Patients with C7 and C8 spine injuries typically suffer full leg paralysis and partial loss of arm and hand functionality, which impairs their ability for a wholesome and independent life. There is currently a variety of assistive driving devices on the market. Spinner knobs with secondary controls allow many such patients to regain their driving ability, opening opportunities to employment and a more diverse and independent lifestyle, leading to a higher-quality life. However, current spinner knobs with secondary controls suffer from (a) inconvenient grip that may induce wrist strain and discomfort in prolonged operation and (b) inconvenient button placement that requires the patient to somewhat release the grip or completely let go of the wheel. Devices that solve these issues, e.g. by an alternate grip style, are, on the other hand, not appropriate for patients that do not have full control of their hands and arms.

SUMMARY

Various implementations include an assistive driving device. The assistive driving device includes a base, a first post, a second post, a third post, and a selector. The first post is for receiving a portion of a palm of a hand of a user. The first post has a proximal end and a distal end opposite and spaced apart from the proximal end. The proximal end of the first post is coupled to the base. The second post has a proximal end and a distal end opposite and spaced apart from the proximal end. The proximal end of the second post is coupled to the base. The third post has a proximal end and a distal end opposite and spaced apart from the proximal end. The proximal end of the third post is coupled to the base. The second post and the third post are positioned to receive a portion of an arm of the user. The selector is spaced apart from the first post and positioned such that the selector is actuatable with a dorsum of the hand of the user.

In some implementations, the base includes a steering wheel mount for coupling the base to a steering wheel of a vehicle. In some implementations, the base is couplable to hand controls of a vehicle.

In some implementations, the selector includes a button. In some implementations, the first post has a surface extending from the proximal end of the first post to the distal end of the first post, and the button being radially spaced apart from the surface of the first post and actuatable by compressing the button in a direction perpendicular to a portion of the surface of the first post.

In some implementations, the first post includes a hinge coupled to the proximal end of the first post and the base, the first post being rotatable about the hinge in a direction of the selector. In some implementations, the first post is rotatable from a first position to a second position. The first post is rotated a rotation angle when the first post is moved from the first position to the second position, wherein the rotation angle is between 0 degrees and 45 degrees.

In some implementations, the device further includes a controller configured to receive a signal from the selector and send a feedback signal to a feedback device for indicating one or more selection options.

In some, implementations, the feedback device, is a display screen for indicating the one or more selection options. In some implementations, the feedback device is a speaker for indicating the one or more selection options.

In some implementations, the controller sends an output signal to a car electronic control unit when a selection option has been selected.

In some implementations, the one or mare selection options are primary controls. In some implementations, the one or more selection options are secondary controls.

Various other implementations include a method of controlling selection options using an assistive driving device. The assistive driving device includes a base, a first post, a second post, a third post, a selector, and a controller. The first post is for receiving a portion of a palm of a hand of a user. The first post has a proximal end and a distal end opposite and spaced apart from the proximal end. The proximal end of the first post is coupled to the base. The second post has a proximal end and a distal end opposite and spaced apart from the proximal end. The proximal end of the second post is coupled to the base. The third post has a proximal end and a distal end opposite and spaced apart from the proximal end. The proximal end of the third post is coupled to the base. The second post and the third post are positioned to receive a portion of an arm of the user. The selector is spaced apart from the first post and positioned such that the selector is actuatable with a dorsum of the hand of the user. The controller is configured to receive a signal from the selector and send a feedback signal to a feedback device for indicating one or more selection options. The controller sends a selection signal to the car electronic control unit when a selection option has been selected.

The method includes (1) electronically coupling an assistive driving device with a car electronic control unit; (2) indicating via the feedback device that one of the selection options is a current option; (3) indicating via the feedback device that another of the selection options is the current option when a skip signal is sent from the controller to the feedback device, wherein the skip signal is sent from the controller to the feedback device when the selector is actuated in a first pattern; and (4) sending a selection signal from the controller to the car electronic control unit when the selector is actuated in a second pattern, wherein the selection signal indicates the selection option that is the current option.

In some implementations, the base includes a steering wheel mount for coupling the base to a steering wheel of a vehicle. In some implementations, the base is couplable to hand controls of a vehicle.

In some implementations, the selector includes a button. In some implementations, the first post has a surface extending from the proximal end of the first post to the distal end of the first post, and the button being radially spaced apart from the surface of the first post and actuatable by compressing the button in a direction perpendicular to a portion of the surface of the first post.

In some implementations, the first post includes a hinge coupled to the proximal end of the first post and the base, the first post being rotatable about the hinge relative to the base and in a direction of the selector. In some implementations, the first post is rotatable to a rotation angle, wherein the rotation angle is between 0 degrees and 45 degrees.

In some implementations, the feedback device is a display screen for indicating the one or more selection options. In some implementations, the feedback device is a speaker for indicating the one or more selection options.

In some implementations, the one or more selection options are primary controls. In some implementations, the one or more selection options are secondary controls.

In some implementations, the first pattern is one of a single compression of the button, a double compression of the button, a triple compression of the button, or a maintained compression of the button. In some implementations, the second pattern is another of a single compression of the button, a double compression of the button, a triple compression of the button, or a maintained compression of the button.

BRIEF DESCRIPTION OF DRAWINGS

Example features and implementations are disclosed in the accompanying drawings. However, the present disclosure is not limited to the precise arrangements and instrumentalities shown.

DETAILED DESCRIPTION

Figure 1A:
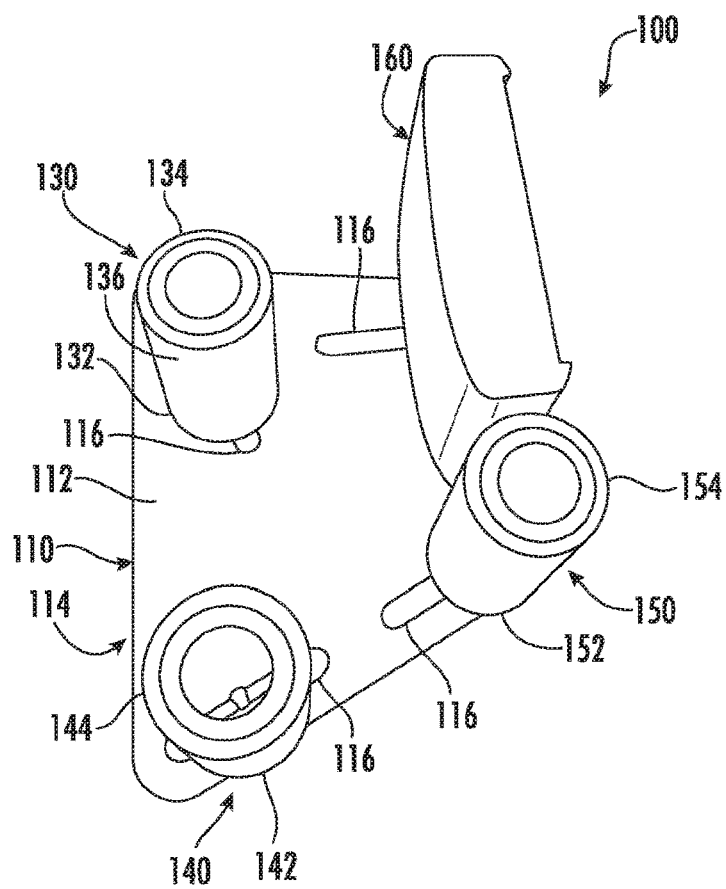
FIGS. 1A and 1B show an assistive driving device, according one implementation.
Figure 1B:
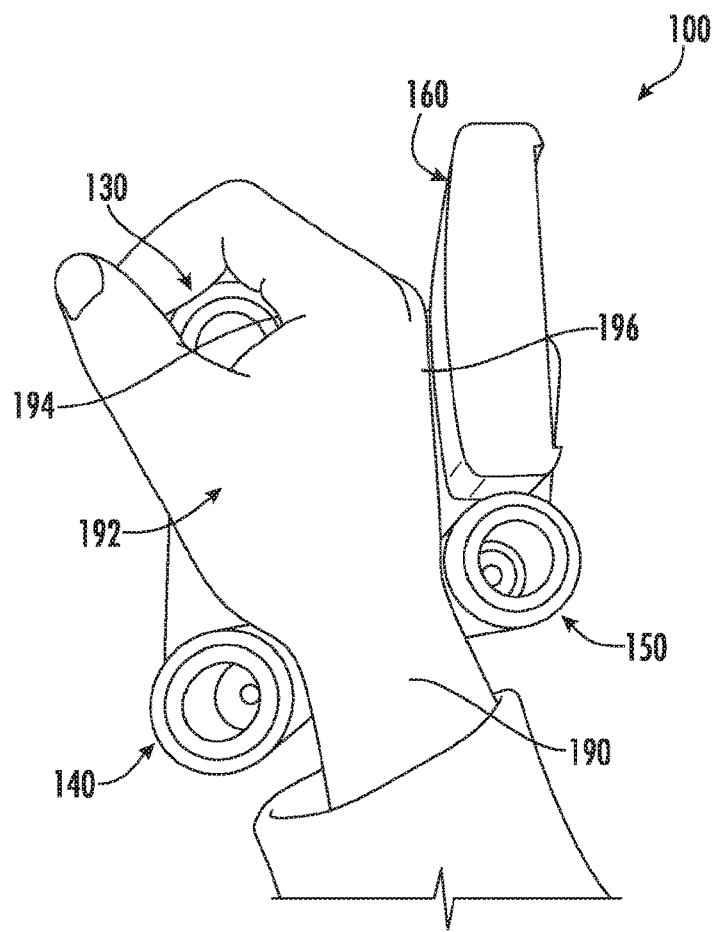
Figure 2A:
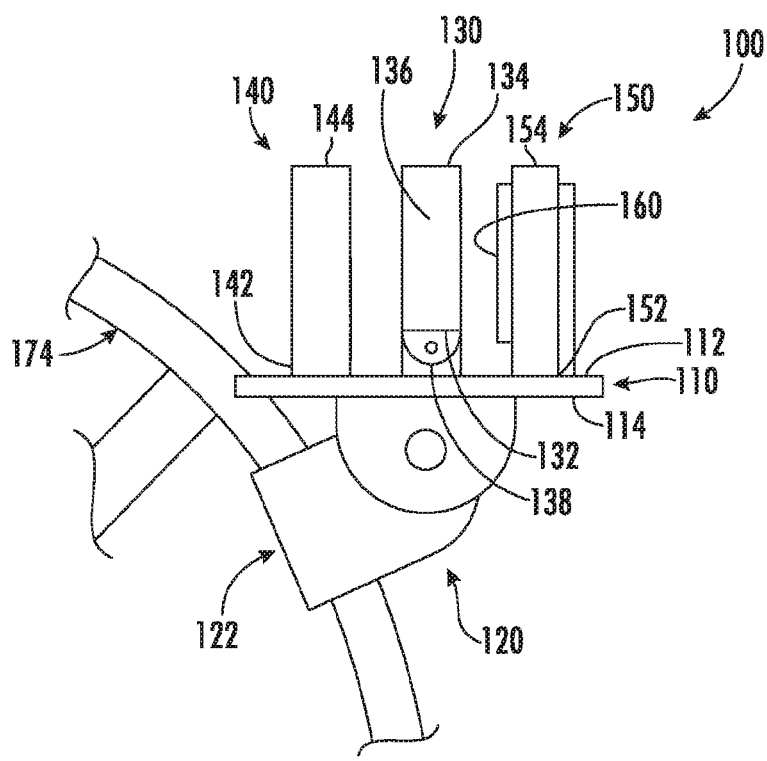
FIGS. 2A and 2B show side views of the assistive driving device of FIG. 1 coupled to a steering wheel of a vehicle.
Figure 2B:
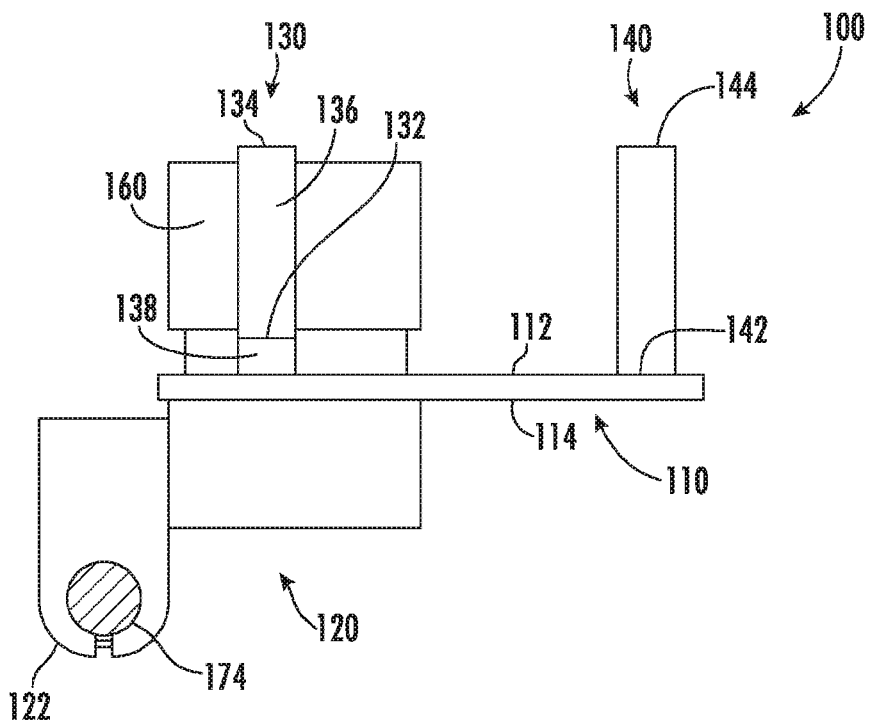

The devices and methods disclosed herein provide for an assistive driving device that allows for an alternative means for controlling various functions of a vehicle. The device is designed to be usable by users who lack fine motor function. The device includes three posts (also called "pins" herein) to secure a user's hand and arm. The forward most post is configured to receive the paint of the hand of the user when the arm of the user is secured between the two back posts. The device is rotatably secured to the steering wheel of a car such that the user can rotate the steering wheel using the device while allowing the device to maintain an upright orientation. The device includes a selector that is actuatable by the dorsum of the hand of the user while the user is holding the forwardmost post. The selector is used to select various selection options to control the functions of the vehicle.

Various implementations include an assistive driving device. The assistive driving device includes a base, a first post, a second post, a third post, and a selector. The first post is for receiving a portion of a palm of a hand of a user. The first post has a proximal end and a distal end opposite and spaced apart from the proximal end. The proximal end of the first post is coupled to the base. The second post has a proximal end and a distal end opposite and spaced apart from the proximal end. The proximal end of the second post is coupled to the base. The third post has a proximal end and a distal end opposite and spaced apart from the proximal end. The proximal end of the third post is coupled to the base. The second post and the third post are positioned to receive a portion of an arm of the user. The selector is spaced apart from the first post and positioned such that the selector is actuatable with a dorsum of the hand of the user.

Various other implementations include a method of controlling selection options using an assistive driving device. The assistive driving device includes a base, a first post, a second post, a third post, a selector, and a controller. The first post is for receiving a portion of a palm of a hand of a user. The first post has a proximal end and a distal end opposite and spaced apart from the proximal end. The proximal end of the first post is coupled to the base. The second post has a proximal end and a distal end opposite and spaced apart from the proximal end. The proximal end of the second post is coupled to the base. The third post has a proximal end and a distal end opposite and spaced apart from the proximal end. The proximal end of the third post is coupled to the base. The second post and the third post are positioned to receive a portion of an arm of the user. The selector is spaced apart from the first post and positioned such that the selector is actuatable with a dorsum of the hand of the user. The controller is configured to receive a signal from the selector and send a feedback signal to a feedback device for indicating one or more selection options. The controller sends a selection signal to the car electronic control unit when a selection option has been selected.

The method includes (1) electronically coupling an assistive driving device with a car electronic control unit; (2) indicating via the feedback device that one of the selection options is a current option; (3) indicating via the feedback device that another of the selection options is the current option when a skip signal is sent from the controller to the feedback device, wherein the skip signal is sent from the controller to the feedback device when the selector is actuated in a first pattern; and (4) sending a selection signal from the controller to the car electronic control unit when the selector is actuated in a second pattern, wherein the selection signal indicates the selection option that is the current option.

FIGS. 1A-2B show an assistive driving device 100. The device 100 includes a base 110, a first post 130, a second post 140, a third post 150, a selector 160, and a controller 170. The base 110 has a first surface 112 and a second surface 114 opposite and spaced apart from the first surface 112. The base 110 has a steering wheel mount 120 coupled to the second surface 114 for coupling the base 110 to a steering wheel 174 of a vehicle. The steering wheel mount 120 includes a clamp 122 for clamping the steering wheel mount 120 around the outer portion of a steering wheel 174 such that the base 110 is coupled to the steering wheel 174. The steering wheel mount 120 is rotatably coupled to the second surface 114 of the base 110 such that the base 110 can rotate relative to the steering wheel 174 when mounted to the steering wheel 174. Because the steering wheel mount 120 is rotatably coupled to the second surface 114 of the base 110, the base 110 can be kept upright in use when the steering wheel 174 is rotated. Although the steering wheel mount 120 shown in FIGS. 2A and 2B includes a clamp 122 for coupling the base 110 to a steering wheel 174, in other implementations, the base is couplable to a steering wheel by a fastener, an adhesive, a tie, or any other coupler capable of securing the base to a steering wheel. In some implementations, the base does not include a steering wheel mount and the device is mounted to another portion of the vehicle such as the hand controls of the vehicle.

Each of the first post 130, the second post 140, and the third post 150 have a proximal end 132, 142, 152 and a distal end 134, 144, 154 opposite and spaced apart from the proximal end 132, 142, 152. The proximal end 132, 142, 152 of each post is coupled to the first surface 112 of the base 110. The second post 140 and the third post 150 are positioned to receive a portion of the arm 190 of a user and are coupled to the base 110 by fasteners disposed in slots 116 defined by the base 110. Each of the second post 140 and third post 150 are adjustable relative to each other by loosening the fasteners, moving the fasteners within the slots 116, and retightening the fasteners. Thus, the second post 140 and third post 150 can be adjusted to receive a variety of widths of arms 190 such that a user's arm 190 can be tightly retained between the second post 140 and third post 150.

The first post 130 has a surface 136 extending from the proximal end 132 of the first post 130 to the distal end 134 of the first post 130, and the surface 136 of the first post 130 is configured to receive a portion of the palm 194 of the hand 192 of a user. The first post 130 includes a hinge 138 coupled to the proximal end 132 of the first post 130, and the hinge 138 is coupled directly to the base 110. The position of the hinge 138, and thus the first post 130, is adjustable relative to the second post 140 and third post 150. The hinge 138 is coupled to the base 110 by a fastener disposed in a slot 116 defined by the base 110. The first post 130 is adjustable relative to the second post 140 and the third post 150 by loosening the fastener, moving the fastener within the slot 116, and retightening the fastener. Thus, the first post 130 can be adjusted relative to the second post 140 and third post 150 to receive a variety of lengths of arms 190 such that a user's arm 190 can be tightly retained between the second post 140 and third post 150 while the user's hand 192 can comfortably reach the first post 130.

The selector 160 is spaced apart from the first post 130 and positioned such that the selector 160 is actuatable with the dorsum 196 of the hand 192 of the user. The selector 160 shown in FIGS. 1A-2B is a button that is actuatable by compressing the button in a direction perpendicular to a portion of the surface 136 of the first post 130. The button is large enough that a person tacking fine motor function can easily actuate the button when desired. The first post 130 is rotatable about the hinge 138 in the direction of the selector 160 such that a user gripping the first post 130 can rotate the first post 130 about the hinge 138 to actuate the selector 160 without releasing the first post 130. The first post 130 is rotatable about the hinge 138 from a first position to a second position such that the first post 130 can be rotated a rotation angle of 45 degrees. The 45-degree rotation angle of the first post 130 shown in FIG. 1 allows the user to rotate the user's wrist or arm 190 to actuate the selector 160. However, in other implementations, the rotation angle is between 0 degrees and 45 degrees. In some implementations, the rotation angle is greater than 45 degrees. Although the selector 160 shown in FIGS. 1A-2B is a button, in other implementations, the selector is a switch, a hinged post, or any other selection device capable of being actuated with the dorsum of the hand of a user when the user is gripping the first post.

The controller 170 is configured to receive a signal from the selector 160 when the selector 160 is actuated and send a feedback signal to a feedback device 180 for indicating one or more selection options 182. The controller 170 sends a selection signal to the car electronic control unit when a selection option 182 has been selected. The controller 170 in FIGS. 3A and 3B sends the selection signal to the car electronic control unit via Bluetooth signal, but in other implementations, the controller is hardwired to the car electronic control unit and the selection signal is sent to the car electronic control unit via hardwire.

Figure 3A:
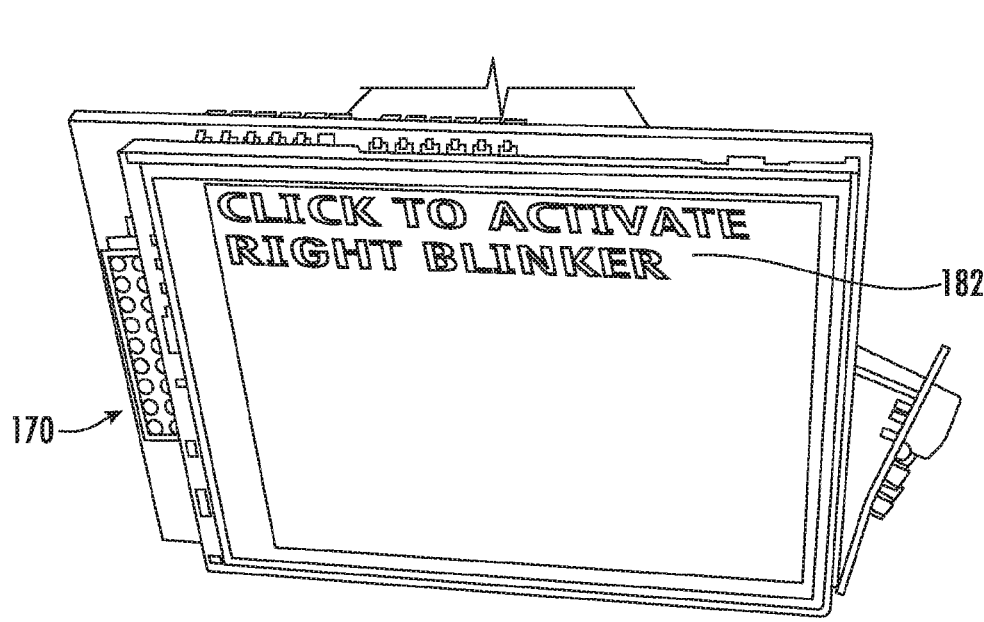
FIGS. 3A and 3B show a feedback device of the assistive driving device of FIG. 1 as a display screen.
Figure 3B:
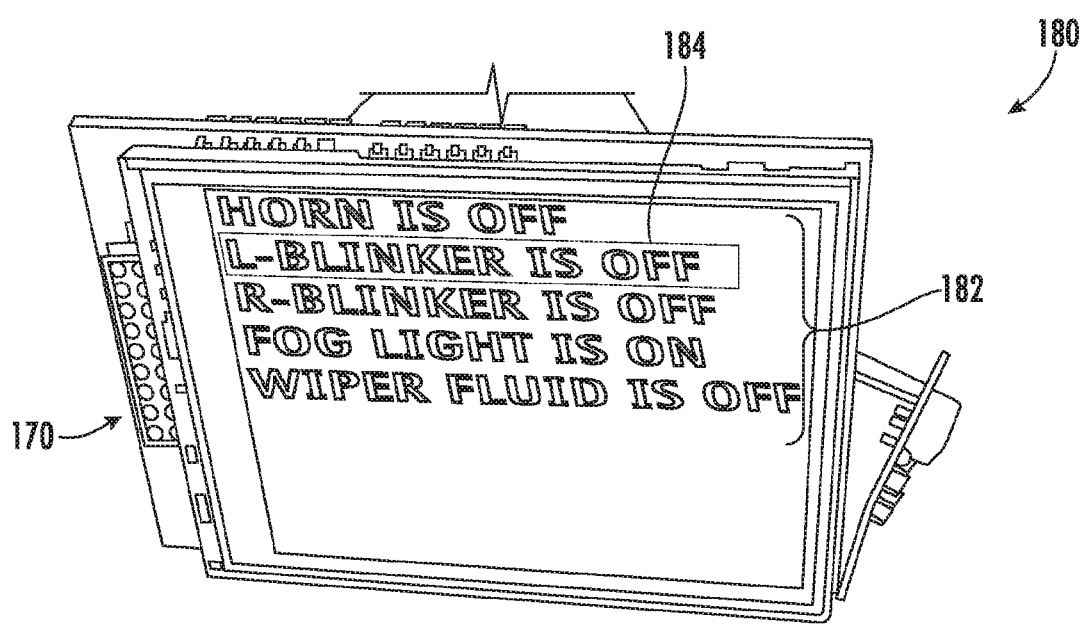

The feedback device 180 shown in FIGS. 3A and 3B is a display screen 180 for indicating the one or more selection options 182. The display screen 180 is a LCD screen, but in other implementations, the screen is [types of screens]. The display screen 180 is coupled to the dashboard of the vehicle, but in other implementations, the vehicle is manufactured with a built-in screen and the built-in screen is the display screen. In other implementations, the vehicle is retrofitted to permanently couple the display screen to the vehicle.

As shown in FIGS. 3A and 3B, the display screen 180 displays a first of selection options 182 with one of the selection options 182 being highlighted to indicate that the highlighted selection option 182 is the current option 184. A user can actuate the selector 160 to change the current option 184 to another selection option 182 and to select a current option 184, as described below.

In other implementations of the device, the feedback device is a speaker for indicating the one or more selection options. In one implementation, the speaker is a speaker installed in the originally manufactured vehicle, but in other implementations, the speaker is incorporated in the device. In some implementations, the speaker is mounted to a portion of the vehicle. In some implementations, the vehicle is retrofitted to permanently couple the speaker to the vehicle.

The speaker indicates the selection options by outputting a voice speaking the selection options and also indicates the selection option that is the current option. However, in other implementations, the speaker can output any other noises to indicate selection options and current option. As with the display screen 180 shown in FIGS. 3A and 3B, a user can actuate the selector to change the current option to another selection option and to select a current option, as described below.

Figure 4:
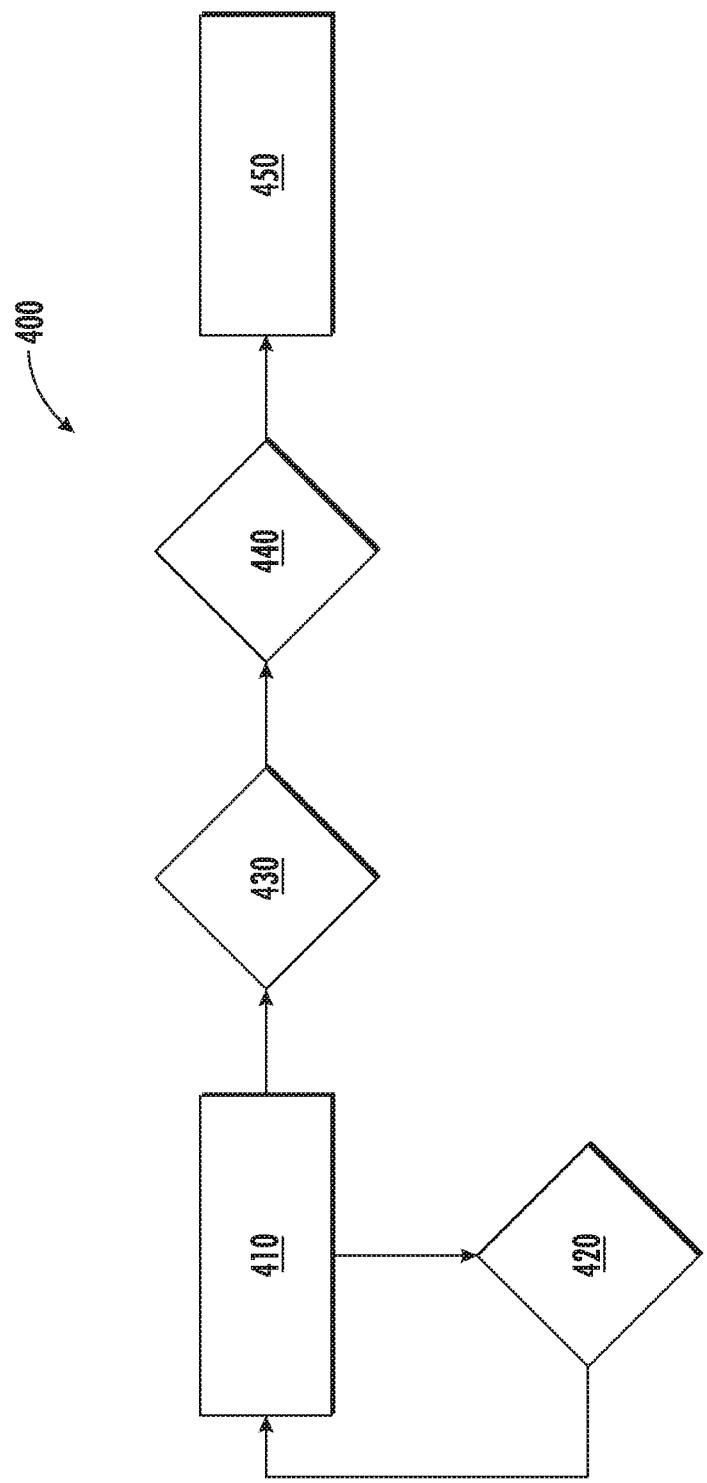
FIG. 4 shows a flow chart of e controls for the assistive driving device of FIG. 1.

FIG. 4 shows a flowchart 400 of a process for the controller 170 to control the feedback device 180 and send signals to the car electronic control unit in response to receiving signals from the selector 160. When the feedback device 180 is powered on, a selection option 182 is highlighted indicate that the selection option 182 is the current option 184, as shown by the first block 410. To switch the current option 184 between different selection options 182, a user actuates the selector 160 in a first pattern, shown in the second block 420. In response to the controller 170 receiving an input signal(s) in the first pattern, the controller 170 sends a skip signal to the feedback device 180, which causes the feedback device 180 to change the current option 184 to another selection option 182. The first pattern can be any pattern of actuating the selector 160, such as a single actuation of the selector, a double actuation of the selector, a triple actuation of the selector, or a maintained actuation of the selector.

To select a selection option 182 that is the current option 184, a user actuates the selector 160 in a second pattern, shown in the third block 430. In response to the controller 170 receiving an input signal(s) in the second pattern, the controller 170 sends a selection signal to the car electronic control unit, shown in the fourth block 440, which causes the car electronic control unit to perform the function indicated by the selection option 182 that is the current option 184, shown in the fifth block 450. The second pattern can be any pattern of actuating the selector 160, other than the first pattern, such as a single actuation of the selector, a double actuation of the selector, a triple actuation of the selector, or a maintained actuation of the selector.

The one or more selection options 182 shown on the display screen 180 in FIGS. 3A and 3B are secondary controls, but in other implementations, the selection options are primary controls. Primary controls are controls that are used in the driving operation of a vehicle. Examples of primary controls include the control of accelerating, braking, shifting, parking, and steering. Secondary controls are controls that are used in a to operate functions of a vehicle other than primary controls. Examples of secondary controls include the control of turn signals, headlights, HVAC, cruise control, car stereo, windshield wipers, and automatic windows.

It should be appreciated that the logical operations described herein with respect to the various figures may be implemented (1) as a sequence of computer implemented acts or program modules (i.e., software) running on a computing device (e.g., the computing device described in FIG. 5), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 5:
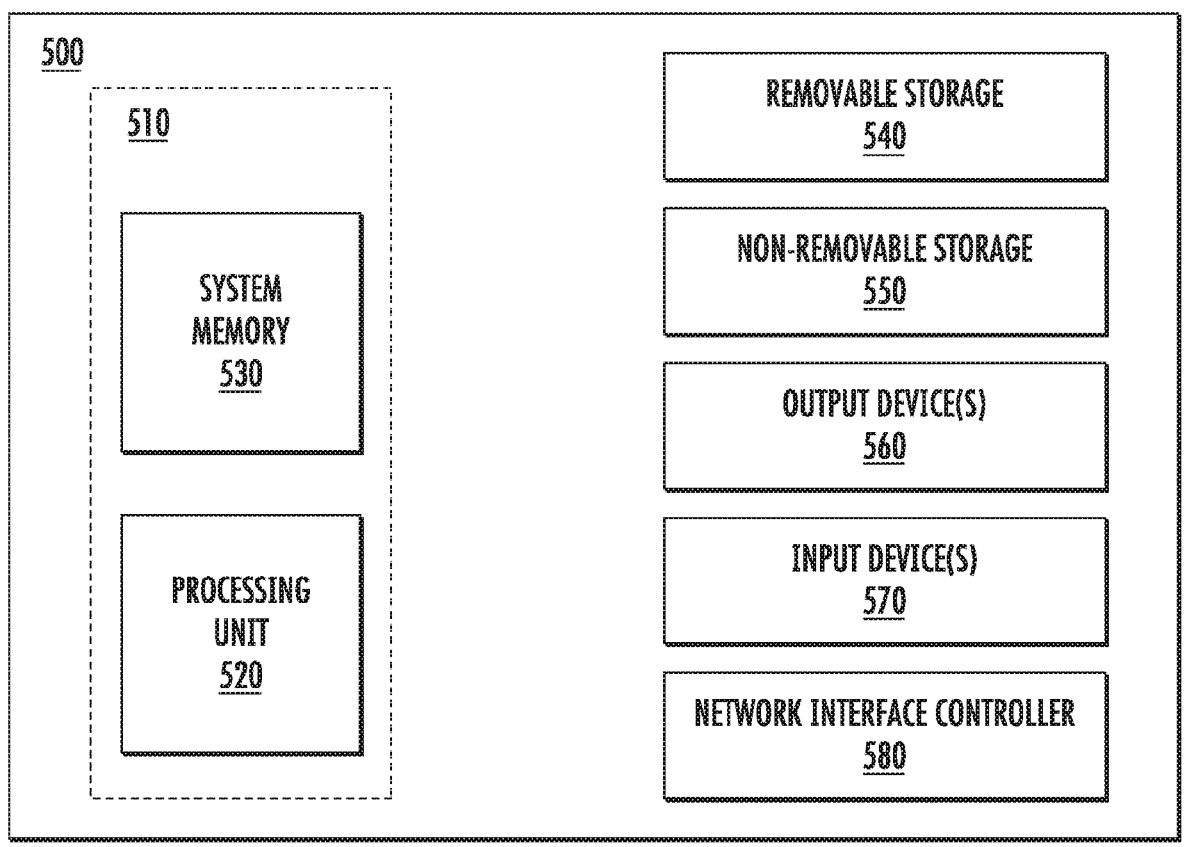
FIG. 5 is an exemplary computer system suitable for implementing one or more controllers.

Referring to FIG. 5, an example computing device 500 upon which embodiments of the invention may be implemented is illustrated. For example, the controller 170 described herein may be implemented as a computing device, such as computing device 500. It should be understood that the example computing device 500 is only one example of a suitable computing environment upon which embodiments of the invention may be implemented. Optionally, the computing device 500 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In an embodiment, the computing device 500 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computing device 500 to provide the functionality of a number of servers that is not directly bound to the number of computers in the computing device 500. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In its most basic configuration, computing device 500 typically includes at least one processing unit 520 and system memory 530. Depending on the exact configuration and type of computing device, system memory 530 may be volatile (such as random access memory (RAM)), non-volatile (such as read-only memory (ROM), flash memory, etc.) some combination of the two. This most basic configuration is illustrated in FIG. 5 by dashed line 510. The processing unit 520 may be a standard programmable processor that performs arithmetic and logic operations necessary for operation of the computing device 500. While only one processing unit 520 is shown, multiple processors may be present. Thus, while instructions may be discussed as executed by a processor, the instructions may be executed simultaneously, serially, or otherwise executed by one or multiple processors. The computing device 500 may also include a bus or other communication mechanism for communicating information among various components of the computing device 500.

Computing device 500 may have additional features/functionality. For example, computing device 500 may include additional storage such as removable storage 540 and non-removable storage 550 including, but not limited to, magnetic or optical disks or tapes. Computing device 500 may also contain network connection(s) 580 that allow the device to communicate with other devices such as over the communication pathways described herein. The network connection(s) 580 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. Computing device 500 may also have input device(s) 570 such as a keyboards, keypads, switches, dials, mice, track balls, touch screens, voice recognizers, card readers, paper tape readers, or other well-known input devices. Output device(s) 560 such as a printers, video monitors, liquid crystal displays (LCDs), touch screen displays, displays, speakers, etc. may also be included. The additional devices may be connected to the bus in order to facilitate communication of data among the components of the computing device 500. All these devices are well known in the art and need not be discussed at length here.

The processing unit 520 may be configured to execute program code encoded in tangible, computer-readable media. Tangible, computer-readable media refers to any media that is capable of providing data that causes the computing device 500 (i.e., a machine) to operate in a particular fashion. Various computer-readable media may be utilized to provide instructions to the processing unit 520 for execution. Example tangible, computer-readable media may include, but is not limited to, volatile media, non-volatile media, removable media and non-removable media implemented in any method or technology for storage of information such as computer readable instructions, data structures, program modules or other data. System memory 530, removable storage 540, and non-removable storage 550 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

In an example implementation, the processing unit 520 may execute program code stored in the system memory 530. For example, the bus may carry data to the system memory 530, from which the processing unit 520 receives and executes instructions. The data received by the system memory 530 may optionally be stored on the removable storage 540 or the non-removable storage 550 before or after execution by the processing unit 520.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Embodiments of the methods and systems may be described herein with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Normal functionality to drive requires imperative cognitive and motor skills that have become second nature for most individuals. The motor skills necessary for driving include: no cognitive impairments, bilateral coordination, manual dexterity, and executive functioning. In addition, a driver must be able to maintain good posture to sit and grip the steering wheel. They must have trunk control to maintain upright in driver's seat, shoulder abduction/flexion to reach the steering wheel, wrist flexion/extension and wrist adduction/abduction to turn the steering wheel and finger flexion to grasp the steering wheel. A combination of all of the above motor skills are necessary to perform remote functions. However, many people with spinal cord injuries or that have limited hand movement cannot control the steering wheel and secondary controls without an assistive driving device with secondary controls. The need for these adaptive devices is immense. SCI is the second leading cause of paralysis in the United. States; it is reported that 1.2 million Americans are living with paralysis resulting from SCI and half of them occur at the cervical area. The implications of SCI or other injuries causing paralysis impacts not only the patient's living and independence but also their families, caregivers, healthcare providers, and employers.

From the population with SCI, the patients with a SCI at the C7 or above have limited, varying movement in the head, neck, shoulders, arms and wrist depending on the type of injury (complete or incomplete) and the location. These individuals can shrug shoulders, bend elbows, turn palms up and down and extend wrists. However, at these SCI levels, the patients lack the ability to have fine motor hand functions. As summarized in FIG. 1 below, the correlation between the level in the spinal cord or location with the parts of the muscles and body the nerve controls. More specifically, injuries from C1-C4 are most severe including not being able to cough, breath or control bowel movements, paralysis in arms, hands, trunk and legs and require complete assistance even for driving. In cases of incomplete spinal cord injury, patients can have more functionality or motor movement of their limbs allowing them to utilize assistive devices to drive. In comparison to spinal cord injuries ranging from C5-C8, these patients can breathe on their own and have control over bowel movements. Injury at these levels correspond to hand and arm nerve damage. Injury at the C5 level, the patient can raise his or her arms and bend elbows; however, it's likely to have some or total paralysis of the legs, wrist, hands and trunk. Injury at the C6 level, the patient should be able to bend wrist back, but typically still has paralysis in hands, trunk and legs. Injury at the C7 level, patients can straighten their arms and have normal movements at their shoulders still allowing them to do most daily activities such as driving with an assistive device. Injury at the C8 level, patients should be able to grasp and release objects and may also drive with an adaptive motor device.

Therefore, the need for an adaptive device to not only steer the wheel but also contain buttons to control remote functions is critical for their ability to drive. The devices described herein help individuals with limited finger flexion to grasp the wheel and perform secondary functions such as windshield wipers, turn signals, radio, horn, and blinkers, but maintain the rest of the required movements and cognitive awareness to drive. The physicians and occupational therapist must determine the individual's ability to perform all of these tasks safely with no fatigue before allowing them to independently drive with assistive devices. The devices disclosed herein help patients that cannot drive a vehicle without an assistive device. Currently, one of the assistive devices that are able to permit this population to drive a vehicle is the spinner knob with secondary controls.

The spinner knobs not only increase the user's odds of employment, but also enhance the user's life by giving them independence and freedom from reliance on others. According to the American Journal of Physical Medicine and Rehabilitation, low independence and mobility had a direct correlation to increased likelihood of depression. The freedom and independence more specifically help these patients with depression to allow them to feel "normal" in society. Unfortunately, SCI survivors' report that sixty percent of their highest pain and weakness in their shoulder, arm and wrist/hand is due to 'self-mobility tasks', The key activity of the self-mobility tasks is driving. These could be contributing to the improperly designed assistive driving devices which could cause the patients pain that could be prevented with a properly designed device. The devices disclosed herein provide a robust steering assist control for all individuals to allow consistent lane-keeping performance, despite variations in driver behavior. Many individuals believe that an adaptive steering device is easier to grip and control a vehicle for all persons, compared to a regular wheel. This means that adaptive equipment can allow individuals the ability to compensate for actions that they have or cannot control through these devices to improve their daily life and independence. The ergonomic spinner knob is a gateway for many individuals with one hand functionality and limitation of fine motor hand movements to drive or continue driving.

The ergonomic spinner knob is vital for individuals that must drive with one hand and can't take their hand off the wheel to engage the secondary functions to regain independence. The ergonomic spinner knob allows individuals to steer their vehicle with the spinner knob and activate the secondary functions (turn signals, lights, wind shield wipers, and horn) by using the triggers placed in reaching distance of their thumb and fingers. The spinner knob is easily portable as well as has the ability to firmly attach and be removed to an adaptable steering for either left or right handed individuals. Further, the secondary buttons can be alternatively wired to perform certain remote functions.

Individuals with spinal cord injuries (SCI) need an assistive device in order to accomplish driving a vehicle. These devices include spinner knobs, spinner knobs with secondary controls, hand controls, mod-tech van, and high-tech vans. Spinner knobs allows individuals that lack the ability to control a steering wheel on their own, the ability to steer the car by providing an easier grip. The purpose of a spinner knob with secondary controls is to permit the driver to control the steering of the vehicle and to activate secondary controls with one hand as the other hand controls the vehicle acceleration and brakes. The mod-tech van and the high-tech van allow individuals with higher level SCI to drive with all gross motor functions such as utilizing their head and elbow. Currently, the spinner knobs with secondary controls require a high level of fine motor function to both grip the device and activate the secondary controls. Individuals with SCI from C7-C8 cannot utilize the current spinner knobs with secondary controls because they lack the finer motor skills needed to use the adaptive driving device. Therefore, these individuals must use the mod-tech vans or high-tech vans allowing them to drive using all gross motor movements. The devices disclosed herein utilize gross motor movements for both steering the wheel and activating the secondary controls addressing the deficiencies of the current devices on the market. This allows the end user to not only drive comfortability but also save thousands of dollars due to the lowered cost of the spinner knob compared to the high-tech vans.

The devices consist of a flat, slotted, metal base plate and four pins mounted onto the slots by the device installer. The user puts their hand into the device with the user's wrist being located between two supporting pins at the bottom of the base plate and the user's thumb palm is held against a third supporting pin that is located in the top middle of the base plate. The fourth pin houses the electronics and contains the main button which the user can activate by means of wrist extension. A pin on the underside of the base plate connects the device to a clamp on the steering wheel of the vehicle, allowing the device to pivot. Steering of the steering wheel occurs in a circular motion of the user's hand without requiring the user to maintain an active grip. A small screen (head-up display) mounted on the dashboard in the user's line of sight displays the menu of vehicular secondary control functions when the user presses the button.

This device does not require any fine motor skills to steer the vehicle and activate the secondary controls. The device has a 'pin' like design to hold the hand and wrist in a comfortable position not requiring any muscular strength keep their hand on the device. The device utilizes one big button that can be activate by gross motor movements. In addition, the device has a visual screen to see the secondary control that would be activated instead of requiring the user to cognitively memorize the secondary controls. The screen and the device communicate wirelessly with each other through the industrial, scientific and medical (ISM) radio bands. Overall, the device provides comfort, no fine motor movements, and cognitive challenges to allow this population to use the device with ease.

The devices disclosed herein are useful for people that must drive with one hand; therefore, they cannot take their hands off the steering wheel or hand control (primary controls) to control secondary functions of the car. More specifically, the devices disclosed herein are useful for individuals with spinal cord injuries from C8 to C6. In addition, any other individuals who have a partial SCI from C5 and up, traumatic brain injury, stroke resulting in hemiplegia, amputees, multiple sclerosis, and paralysis who cannot control a standard steering wheel may also benefit from a new assistive driving device.

The devices described, herein are safe for the user. More specifically, the devices do not negatively impact the driving capabilities of the user such as by distracting the user or interfering with other vehicular equipment. In addition, the devices are safe for the public. The devices do not impact other vehicles or impair other drivers' ability to operate their vehicle. Also, the devices are durable, so they will not fail or malfunction while the user is operating them as device failure would put both the user and others in an unsafe situation.

The devices are also comfortable for the user. The user utilizes their hand, wrist and forearm in order to grasp and use the devices, so it is necessary that the user is put in a comfortable position throughout the duration of the user's driving period. If the user's hand position is uncomfortable, it could possibly induce injuries such as strained tendons leading to carpal tunnel. In addition, the devices are portable. This allows the user to easily use the devices in multiple vehicles and permit other drivers of the user's vehicle (such as family members) to remove a device in order to operate the vehicle without it.

Also, to allow the clinical population to easily use the devices, the devices are adaptive. More specifically, the devices are able to be adaptable to each user's diverse conditions. Users with different finger and/or wrist functionality should both be able to use the devices. Also, the devices are intuitive in order for easy secondary control recognition and learning purposes.

Lastly, the devices are inexpensive. This is important, because the more inexpensive the devices are, the more users that are able to afford and benefit from the devices. In addition, the low costs of the devices make the devices more competitive with the current market.

The devices abide by the current laws and standards that govern assistive steering wheel and secondary controls devices as well as laws and standards pertaining to the safety. In addition, certain states have different state laws pertaining to these devices. Therefore, the devices are able to follow these laws as well. In addition, the device cost equal to or less than similar devices on the market, which is in the range of $500-$1000 in order for the devices to be competitive and affordable to users. The devices are also able to work with the current assistive driving wheels on the market. The devices do not place the user in a poor ergonomic position that can induce other injuries that could result from the devices' uses such as carpal tunnel. Lastly, the devices' sizes/positioning remain within the circumference of the vehicular driving wheel or in the plane of hand control use as not to interfere with other vehicle equipment or the user.

The devices disclosed herein are essential for the clinical population. The current devices on the market do not allow the user to drive and operate the secondary controls of the vehicle as safe as possible. This is due to the current assistive driving devices positioning the user in non-ergonomic hand/wrist positions which causes pain or requiring them to let go of the device/wheel in order to activate a secondary vehicle functions. Therefore, the devices disclosed herein provide individuals in the clinical population not only a safer driving device, but also an increased quality of life.

The devices do not interfere with other electronics. For instance, the devices do not interfere with other vehicle's secondary controls. This functions to prevent the devices from impacting other drivers control of their vehicle in addition to any critical electronic equipment around the devices when they is in use. The devices meet the IEEE 802.15.1 standard which specifies wireless functionality requirements and desired wavelengths. This standard is described in more depth below.

The devices meet the current standards for assistive driving devices. This functions to force the devices to conform to the current accepted safety criteria that has been defined by outside groups and organizations. Thus, the devices meet the Standards for Automotive Adaptive Equipment. This standard is described in more depth below.

The devices are installable/mountable within the circumference of the steering wheel or in the plane of hand control use. This functions to prevent the device from physically interfering with other vehicular equipment and/or be entangled with the users clothing and/or jewelry, all of which could cause the user to lose control of vehicle. The device meets the OSHA1926.602(c)(1)(iv) regulation.

The devices are able to withstand daily use. Therefore, the devices meet the life cycle requirements of assistive driving devices. This in turn is equal to or better than the life time of the car. Thus, the devices are able to function properly for up to ten years. In addition, the devices support the loads that the user may apply to it. Examples of these loads include, but are not limited to the forces applied from turning the wheel, braking the car and installing/uninstalling the devices. This functions to prevent the devices from failing or malfunctioning on the user as that could cause harm to the user, the driver, and the public, other drivers or pedestrians.

The devices position the secondary control "triggers" within close proximity to the user's fingers. Moreover, the user can activate the secondary controls without removing their hand from the device. The user removing their hand from the device is a safety concern as they will in turn lose control of the steering wheel or hand control and ultimately the vehicle.

The devices work in conjunction with current adaptive steering wheels on the market. More specifically, the devices are able to be inset and lock into the current assistive steering wheels. Once the devices are inserted and locked into the wheel, the user is able to manipulate the steering wheel or hand control in order to change the direction of the vehicle while driving through the device.

The devices are able to communicate with the user's vehicle in order to operate the secondary functions. Thus, the desired user input (desired secondary control) results in the device transmitting this input to the vehicle to perform the correct vehicular output (lights turn on off, blinker flashes, etc.). This function allows the user to operate the secondary functions of the vehicle without using the standard physical controls on the vehicle itself.

The devices are ergonomically positioned for the user's hand/wrist. More specifically, the devices maintain an ergonomic hand/wrist position throughout all driving motions. In addition, the devices do not induce pain in the user's wrist/hand for up to three hours of use. This functions to allow the user to comfortably use the device and addresses problems seen with the current assistive devices available on the market.

The devices adapt to diverse user finger functionality. The devices are fully functional with any three fingers on one hand that have motor function. This design function allows the entire clinical population, who have varying motor functionality across their fingers, to utilize the devices as the devices are not limited to users who possess motor functionality in certain fingers (thumb, index finger, etc.).

In some implementations, the devices' secondary control "triggers" are labeled. This functions to allow the user to be able to distinguish between the different controls easily and efficiently. In addition, this functions to promote an easier learning period for the user to remember which "trigger" does which secondary control function. Thus, the devices do not allow a user to incorrectly activate a secondary control five or more times during a time period of fifteen minutes after ten minutes of training from an occupational therapist.

The devices are able to be installed/uninstalled easily and efficiently. More specifically, the devices are able to install or uninstall in under five minutes, as the current devices are able to be installed/uninstalled in below or up to this time period. This function additionally allows the device to be removed easily in order for the vehicles other users to operate the vehicle's steering wheel normally. Moreover, this function addresses the portability objective as well.

The devices also fit inside a vehicle's glove compartment. Thus, the dimensions of the devices are less than a standard glove compartment's dimensions. This allows the devices to be portable as they could easily be stored inside the glove compartment when not in use.

A priority of any automotive device is to maximize safety of drivers and passengers on the road, and any device that compromises safety in any way would not be allowable. The devices meet the standards listed in the Standards for Automotive Adaptive Equipment. The mentioned standards describe the design requirements for automotive adaptive equipment with secondary controls. As outlined in Section 4.1.2.1A of these guidelines, any attachment to a steering wheel must not impede visibility of the road or any devices on the dashboard and any assistive steering device must be removable by an able driver who may have to operate the vehicle. Additionally, Section 4.2 of this standards outlines an array of applications specific to secondary controls. Secondary adaptive equipment must be available to a disabled driver behind the wheel, while also maintaining usability for any operator of the vehicle that may arise.

Additionally, devices cannot be designed that would educe the life of the vehicle and cannot be made with materials that would significantly, permanently degrade after use. Lastly, devices should function under all reasonable environments the vehicle might be in, ranging from temperature to road conditions. Laws seen in these Standards will vary from state to state, so it is important that care is taken so that the device is suitable for use throughout the United States.

ISO 6358:2016 describes the ergonomics principle in the design of work systems. It provides guidelines for the development, realization and implementation for the design of ergonomic work systems.

In come implementations, the devices connect to the CAN system of the car via Bluetooth, and the devices meet the specifications formalized by the Bluetooth Special Interest Group. In addition, the devices also meet standard IEEE 802.15.1. The standard provides detailed guidelines for wireless connectivity with fixed, portable and moving devices within personal operating spaces. For example, the standard specifies that the signal modulation is Gaussian frequency shift keying with a bandwidth-bit period product of 0.5. In addition, the binary one shall be represented by a positive frequency domain. The binary zero shall be represented by a negative frequency deviation.

Assistive devices are usually expected to have the same lifetime as the vehicle they are fitted into. Considering the average consumer car on the road today is 11.6 years old (consistently over 11 years-old over the last 6 years) 17, the devices disclosed herein are designed to last accordingly.

Most spinner knobs on the market today have body parts made of plastic, with metal elements at high-stress points, such as the pinion and the clamp. In the design of the disclosed spinner knob device, the environmental impacts of the materials used are considered, in terms of material production, recyclability and disposal.

Plastics can be used in the devices for ergonomic components of the knob that may require complex shapes. Comparing three plastics commonly used in appliances, HDPE, PET and PVC, PET leads as a fully-recyclable plastic, but at the same time results in most $CO_2$ emission per unit mass produced (3.4 tCO2/t in 2009). Both PVC and HDPE are partially recyclable and generate lower amounts of $CO_2$ in production (1.9 tCO2/t in 2009) [data adapted from Hopewell3]. Biodegradable plastics are advantageous; however, they tend to have inferior material properties. By material properties, both aluminum and steel can be used for metal components; however, there are differences in the carbon footprint of material production. If newly-generated material is used in metal components, steel would produce circa-25% less $CO_2$ emissions than aluminum, whereas the use of fully-recycled aluminum produces less than half of the $CO_2$ footprint by the use of fully-recycled steel [data adapted from Ungureanu12]. Both steel and aluminum can be recycled continuously with no degradation to properties.

A number of example implementations are provided herein. However, it is understood that various modifications can be made without departing from the spirit and scope of the disclosure herein. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. Although the terms "comprising" and "including" have been used herein to describe various implementations, the terms "consisting essentially of" and "consisting of" can be used in place of "comprising" and "including" to provide for more specific implementations and are also disclosed.

Disclosed are materials, systems, devices, methods, compositions, and components that can be used for, can be used in conjunction with, can be used in preparation for, or are products of the disclosed methods, systems, and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a device is disclosed and discussed each and every combination and permutation of the device, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

What is claimed is:

1. An assistive driving device comprising:
   a base;
   a first post for receiving a portion of a palm of a hand of a user, the first post having a proximal end and a distal end opposite and spaced apart from the proximal end, the proximal end of the first post being coupled to the base;
   a second post having a proximal end and a distal end opposite and spaced apart from the proximal end, the proximal end of the second post being coupled to the base;
   a third post having a proximal end and a distal end opposite and spaced apart from the proximal end, the proximal end of the third post being coupled to the base, wherein the second post and the third post are positioned to receive a portion of an arm of the user; and
   a selector spaced apart from the first post and positioned such that the selector is actuatable with a dorsum of the hand of the user.

2. The device of claim 1, wherein the base includes a steering wheel mount for coupling the base to a steering wheel of a vehicle.

3. The device of claim 1, wherein the base is couplable to hand controls of a vehicle.

4. The device of claim 1, wherein the selector comprises a button.

5. The device of claim 4, wherein the first post has a surface extending from the proximal end of the first post to the distal end of the first post, and the button being radially spaced apart from the surface of the first post and actuatable by compressing the button in a direction perpendicular to a portion of the surface of the first post.

6. The device of claim 1, wherein the first post comprises a hinge coupled to the proximal end of the first post and the base, the first post being rotatable about the hinge in a direction of the selector.

7. The device of claim 6, wherein the first post is rotatable from a first position to a second position, wherein the first post is rotated a rotation angle when the first post is moved from the first position to the second position, wherein the rotation angle is between 0 degrees and 45 degrees.

8. The device of claim 1, further comprising a controller configured to receive a signal from the selector and send a feedback signal to a feedback device for indicating one or more selection options, wherein the feedback device is a display screen or a speaker for indicating the one or more selection options.

9. The device of claim 8, wherein the controller sends an output signal to a car electronic control unit when a selection option has been selected.

10. The device of claim 8, wherein the one or more selection options are primary controls or secondary controls.

11. A method of controlling selection options using an assistive driving device, the method comprising:
    electronically coupling an assistive driving device with a car electronic control unit, the assistive driving device comprising:
      a base,
      a first post for receiving a portion of a palm of a hand of a user, the first post having a proximal end and a distal end opposite and spaced apart from the proximal end, the proximal end of the first post being coupled to the base,
      a second post having a proximal end and a distal end opposite and spaced apart from the proximal end, the proximal end of the second post being coupled to the base,
      a third post having a proximal end and a distal end opposite and spaced apart from the proximal end, the proximal end of the third post being coupled to the base, wherein the second post and the third post are positioned to receive a portion of an arm of the user,
      a selector spaced apart from the first post and positioned such that the selector is actuatable with a dorsum of the hand of the user, and
      a controller configured to receive a signal from the selector and send a feedback signal to a feedback device for indicating one or more selection options, wherein the controller sends a selection signal to the car electronic control unit when a selection option has been selected;
    indicating via the feedback device that one of the selection options is a current option;
    indicating via the feedback device that another of the selection options is the current option when a skip signal is sent from the controller to the feedback device, wherein the skip signal is sent from the controller to the feedback device when the selector is actuated in a first pattern; and
    sending a selection signal from the controller to the car electronic control unit when the selector is actuated in a second pattern, wherein the selection signal indicates the selection option that is the current option.

12. The method of claim 11, wherein the base includes a steering wheel mount for coupling the base to a steering wheel of a vehicle.

13. The method of claim 11, wherein the base is couplable to hand controls of a vehicle.

14. The method of claim 11, wherein the selector comprises a button.

15. The method of claim 14, wherein the first post has a surface extending from the proximal end of the first post to the distal end of the first post, and the button being radially spaced apart from the surface of the first post and actuatable by compressing the button in a direction perpendicular to a portion of the surface of the first post.

16. The method of claim 11, wherein the first post comprises a hinge coupled to the proximal end of the first post and the base, the first post being rotatable about the hinge relative to the base and in a direction of the selector.

17. The method of claim 16, wherein the first post is rotatable to a rotation angle, wherein the rotation angle is between 0 degrees and 45 degrees.

18. The method of claim 11, wherein the feedback device is a display screen or a speaker for indicating the one or more selection options.

19. The method of claim 11, wherein the one or more selection options are primary controls or secondary controls.

20. The method of claim 14, wherein the first pattern and/or the second pattern is one of a single compression of the button, a double compression of the button, a triple compression of the button, or a maintained compression of the button.

* * * * *